United States Patent [19]

McGill, III

[11] Patent Number: 5,625,065

[45] Date of Patent: Apr. 29, 1997

[54] STEREOSELECTIVE PROCESS FOR MAKING ENDO-TROPANAMINE AND LIKE COMPOUNDS

[75] Inventor: John M. McGill, III, Lafayette, Ind.

[73] Assignee: Eli Lilly and Company, Indianapolis, Ind.

[21] Appl. No.: 431,379

[22] Filed: Apr. 28, 1995

Related U.S. Application Data

[63] Continuation-in-part of Ser. No. 265,992, Jun. 27, 1994, abandoned.

[51] Int. Cl.$^6$ .................... C07D 451/02; C07D 451/06
[52] U.S. Cl. .............................. 546/124; 546/126
[58] Field of Search ............................... 546/124

[56] References Cited

U.S. PATENT DOCUMENTS 4,921,982   5/1990   Cohen et al. ........................ 549/412

OTHER PUBLICATIONS

Robertson, et al., *J. Med. Chem.*, 35, 310–319 (1992).

Abdel–Magid and Maryanoff, *Syn. Lett.*, 537–539 (1990).

Abdel–Magid, et al., *Tet. Lett.*, 31 (39), 5595–5598 (1990).

Hutchins, et al., *J. Org. Chem.*, 48, 3412–3422 (1983).

Gribble and Nutaitis, *Org. Prep. Proced. Int.*, 17 (4–5), 317–384 (1985).

*Primary Examiner*—Alan L. Rotman
*Attorney, Agent, or Firm*—Robert D. Titus; Joseph A. Jones; David E. Boone

[57] ABSTRACT

A stereoselective process for forming compounds related to 4-endotropanamine through the reactive amination of a corresponding ketone with a triacyloxy borohydride.

8 Claims, No Drawings

STEREOSELECTIVE PROCESS FOR MAKING ENDO-TROPANAMINE AND LIKE COMPOUNDS

CROSS-REFERENCE

This application is a continuation-in-part of U.S. application Ser. No. 08/265,992, filed Jun. 27, 1994, abandoned.

FIELD OF THE INVENTION

This invention relates to a process for making tropanamine and other similar compounds, and will have particular application to the stereoselective production of the endo-isomer of such compounds.

BACKGROUND OF THE INVENTION

Endo-tropanamine is an important structural moiety of zatosetron maleate, a potent antagonist of the 5-hydroxytryptamine (5-HT$_3$) receptor. The structure of zatosetron maleate is disclosed in U.S. Pat. No. 4,921,982 and others and is as shown below.

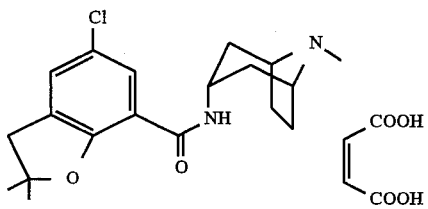

Zatosetron Maleate

The endo-form of tropanamine is the preferred isomer for forming zatosetron maleate. In practice, zatosetron which has the exo-isomer of tropanamine is nearly inactive. As such, during the tropanamine synthesis it is necessary to remove as much of the exo-isomer as possible before reacting the tropanamine with the furan acid chloride intermediate to form zatosetron.

Unfortunately, existing methods of synthesizing tropanamine generate large quantities of the exo-isomer which must be separated prior to the zatosetron forming step of the process. In practice, the current methods of forming tropanamine result in the formation of between 10% and 20% of the exo-isomer which had to be removed by chromatographic and/or recrystallization procedures. This adds a step to the process and is costly and inefficient on a large scale basis.

Since it is desirable to simply carry the tropanamine forward to the zatosetron forming step (without further analysis or separation) a method had to be developed which would stereoselectively form a very high percentage of endo-tropanamine.

The previously accepted method of producing tropanamine-like compounds involved the catalytic hydrogenation of a Schiff base which was derived by reacting tropinone with benzylamine. While this procedure suggested that the equatorial face attack of the reagent would produce high stereoselectivity for the endo-isomer, in practice only an 8 to 1 or 9 to 1 ratio of endo/exo was formed, and poor yields were often the result (60%–70%). Since the overall yield was reduced even further by the separation step, it was highly desirous to discover a novel and more efficient synthesis for tropanamine and related compounds which gave high yields and was highly stereoselective.

SUMMARY OF THE INVENTION

The present invention provides a process for stereoselectively preparing a compound of the formula

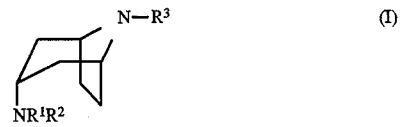

wherein $R^1$ and $R^2$ are independently phenyl, $C_1$-$C_4$ alkyl, phenyl-$C_1$-$C_4$ alkyl or hydrogen, provided that no more than one of $R^1$ and $R^2$ is hydrogen, and wherein phenyl groups are substituted with 0–2 $C_1$-$C_3$ alkyl or $C_1$-$C_3$ alkoxy groups; $R^3$ is hydrogen, a nitrogen protecting group, phenyl, $C_1$-$C_3$ alkyl, or phenyl-$C_1$-$C_3$ alkyl, wherein phenyl groups are substituted with 0–2 $C_1$-$C_3$ alkyl or $C_1$-$C_3$ alkoxy groups; comprising the steps of a) providing a quantity of a compound of the formula

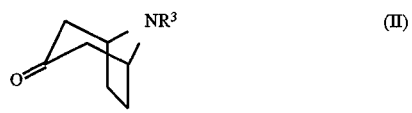

b) reducing the compound of formula II with an amine of the formula $HNR^1R^2$ in the presence of a triacyloxy borohydride salt of the formula $NaBH(OR^4)_3$ to form the endo-isomer of the compound of formula I, wherein $R^4$ is $C_4$-$C_{10}$ α-branched alkanoyl.

Another aspect of the process is that in which the product of formula I is further treated to remove $R^1$ and $R^2$ groups which are other than hydrogen to prepare the compound of the formula

Still another aspect of the invention comprises the new reagents sodium tri(2-ethylhexanoyloxy) borohydride and sodium tri(2-ethylbutanoyloxy) borohydride.

DETAILED DESCRIPTION OF THE INVENTION

The process of this invention achieves the desired results of high yields (approx. 85%) and stereoselectivity (93%–98%) for the endo-isomer. Analysis of the product of formula I or III confirms the high yield and stereoselectivity, which allows for the elimination of the purification and recrystalliization step. Further, when tropanamine is to be prepared, $R^1$ and $R^2$ are preferably hydrogen and benzyl, and benzyl may be removed by a final hydrogenolysis step in an aqueous medium, which further simplifies the procedure and allows for a one-pot conversion. The substantially stereoselectively pure endo-tropanamine is carried forward into the zatosetron synthesis without further isolation.

The chemical names used in the above description are used in their usual meanings. For example, the terms $C_1$-$C_3$ alkyl and $C_1$-$C_4$ alkyl include groups such as methyl, ethyl, propyl, isopropyl, butyl and isobutyl. The term $C_1$-$C_3$ alkoxy includes $C_1$-$C_3$ alkyl groups linked through an oxygen atom. Substituted phenyl groups include such groups as 4-methylphenyl, 3-propoxyphenyl, 2-methyl-5-ethoxyphenyl, 3,5-diethylphenyl, and 3-isopropyl-6-methylphenyl.

Amines of the formula $HNR^1R^2$ include, most preferably, benzylamine, and also include, for example, diethylamine, phenethylamine, 4-methoxyphenylamine, di(3-phenylpropyl)amine, isopropyl-(3,5-dimethylphenyl)amine, and 4-(3,5-diethylphenyl)-butylamine.

Useful $C_4$-$C_{10}$ α-branched alkanoyl groups include, for example, isobutanoyl, 2-ethylpentanoyl, 2-methylhexanoyl, pivaloyl, neopentanoyl, 2-propylhexanoyl, 2,2-diethylpentanoyl and the like.

The term "nitrogen protecting group" is used herein as it is frequently used in synthetic organic chemistry, to refer to a group which will prevent a nitrogen atom from participating in a reaction carried out on some other functional group of the molecule, but which can be removed when it is desired to do so. Such groups are discussed by T. W. Greene in chapter 7 of *Protective Groups in Organic Synthesis*, John Wiley and Sons, N.Y., 1981, and by J. W. Barton in chapter 2 of *Protective Groups in Organic Chemistry*, J. F. W. McOmie, ed., Plenum Press, N.Y., 1973. Examples of such groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred nitrogen protecting groups are benzyl (—$CH_2C_6H_5$), acyl [C(O)R] or $SiR_3$ where R is $C_1$-$C_4$ alkyl, halomethyl, or 2-halo-substituted-($C_2$-$C_4$ alkoxy).

Certain reagents and aspects of the invention are preferred, although all aspects as generally described above are useful and desirable. Each of the following descriptions states a preferred aspect of the invention, and it will be understood that the individual descriptions can be combined to describe additional more limited or more extensive preferred aspects of the invention.

a) $R^1$ is hydrogen;
b) $R^2$ is benzyl;
c) $R^1$ and $R^2$ are independently hydrogen or phenyl-$C_1$-$C_4$ alkyl;
d) $R^1$ and $R^2$ are independently hydrogen or substituted phenyl-$C_1$-$C_4$ alkyl;
e) $R^1$ and $R^2$ are independently hydrogen or $C_1$-$C_4$ alkyl;
f) $R^3$ is $C_1$-$C_3$ alkyl or a nitrogen protecting group;
g) $R^3$ is hydrogen or phenyl;
h) $R^3$ is $C_1$-$C_3$ alkyl;
i) $R^4$ is 2-ethylhexanoyl or 2-ethylbutanoyl;
j) $R^4$ is $C_4$-$C_8$ α-branched alkanoyl;
k) $R^4$ is $C_6$-$C_{10}$ α-branched alkanoyl.

Prior art reductive aminations using, for example, sodium triacetoxy borohydride, produce a substantial amount of an amide byproduct which is difficult to remove from the product. Use of the present bulky reagents further improve the yield and purity of the product by avoiding that amide impurity.

The process of this invention involves the stereoselective preparation of amine derivatives of formula I through the reductive amination of the corresponding ketone. This process is particularly useful in the reductive amination of tropinone to produce tropanamine and particularly the endo-isomer of 4-tropanamine, whose formula is shown below:

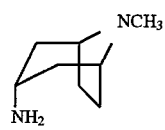

In the most preferred process, the starting material is 4-tropinone which has the following structure

It should be noted that the process of this invention is not limited to this material, but will have application to the stereoselective reductive amination of other ketone compounds of formula II to the corresponding amine derivative.

The basic scheme for producing endo-4-tropanamine and other valuable products according to the process of this invention is shown below as Scheme I:

Scheme I

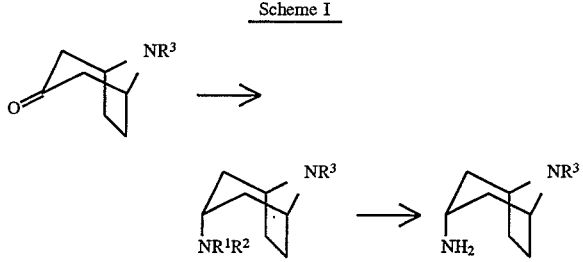

The first step of the above scheme constitutes an invention in itself, and is a preferred aspect of the invention. The products of the first step may be isolated and used in further synthesis or for other purposes. The second step, producing the primary amine, is carried out according to conventional methods, depending on the nature of the $R^1$ or $R^2$ group, and completes the present invention when the objective of the process is to prepare such primary amines. For example, when the amine used in the reductive amination is benzylamine, the final step may conveniently be a hydrogenolysis, which will be discussed below.

When the $R^3$ group is a nitrogen protecting group, a still further step of the process may be a deprotection, carried out by a method appropriate to the individual protecting group, in order to obtain the final product where $R^3$ is hydrogen.

The reductive amination is preferably carried out in a halogenated alkane solvent, such as chloroform, trichloroethane and, most preferably, dichloroethane or dichloromethane. The reaction proceeds in most cases in moderate periods of time such as from a few hours to a day at ambient temperature and pressure.

The sodium triacyloxy borohydride may be prepared in situ by mixing appropriate quantities of sodium borohydride and the appropriate carboxylic acid. The carboxylic acids include, of course, such substances as isobutyric acid, pivalic acid, 2-ethylbutyric acid, 2-ethylhexanoic acid and the like. The reducing agent may also be prepared in advance and added to the reaction mixture, but such is not preferred.

When the reductive amination has gone to the desired degree of completion, the reaction mixture is usually quenched by addition of a moderately strong base, such as aqueous sodium or potassium hydroxide, and the layers are separated. The product of the reductive amination is then found in the organic layer, which is then washed with aqueous acid. The product is then in the aqueous layer, and may conveniently be carried to the second step of the process without isolation. In the most preferred instance, where $R^1$ is hydrogen and $R^2$ is benzyl, the benzyl group may be removed by hydrogenolysis in the aqueous layer, as shown in the examples below. The hydrogenolysis step may be carried out in standard fashion as by bubbling hydrogen gas through a solution of endo-N-benzyl-tropanamine dissolved in a protic solvent (such as an alcohol). This process generally requires the presence of a catalyst such as finely divided platinum or palladium metal on carbon. High catalyst loads (up to 50% by weight) may be required by the prior process to obtain sufficiently high yields.

The following examples are indicative of the process of this invention as used to produce endo-4tropanamine from 4-tropinone.

EXAMPLES 1–4

The following reagents were added to a 500 ml three-necked flask equipped with a stirrer and connected to a reflux condenser and a nitrogen purge. The amounts for each reagent are given in grams (millimoles) (weight equivalents)

Example 1

| REAGENT | |
|---|---|
| $NaBH_4$ | 3.78 (100) (2.0) |
| Isobutyric acid | 30.8 (350) (7.0) |
| $CH_2Cl_2$ (Solvent) | 200 ml |

Example 2

| REAGENT | |
|---|---|
| $NaBH_4$ | 3.78 (100) (2.0) |
| Pivalic acid | 35.75 (350) (7.0) |
| $CH_2Cl_2$ (Solvent) | 200 ml |

Example 3

| REAGENT | |
|---|---|
| $NaBH_4$ | 3.78 (100) (2.0) |
| 2-Ethylbutyric acid | 40.65 (350) (7.0) |
| $CH_2Cl_2$ (Solvent) | 200 ml |

Example 4

| REAGENT | |
|---|---|
| $NaBH_4$ | 3.78 (100) (2.0) |
| 2-Ethylhexanoic acid | 50.5 (350) (7.0) |
| $CH_2Cl_2$ (Solvent) | 200 ml |

In each of the Examples 1–4, the acid reagent was added to the flask via syringe pump over a period of 3–4 hours and the reaction stirred under nitrogen atmosphere until hydrogen evolution was completed.

In all examples, 6.95 grams (50 mmoles, 1.0 equiv.) of 4-tropinone and 8.0 grams (75 mmoles, 1.5 equiv.) of benzylamine were added and stirred under a nitrogen atmosphere until gas chromatography analysis indicated that the reaction was complete (about 18 hours).

In all examples, the reaction was quenched by slow addition of 200 ml of 5 M NaOH. The mixture was stirred for thirty minutes, and the organic layer separated and washed with 200 ml of 5 M NaOH then extracted with 80 ml of 2 M HCl. The aqueous layer of this mixture was then separated and the pH adjusted to 9.0 with 50% NaOH solution.

In all cases, the aqueous layer, which contained benzyl-tropanamine was transferred into a Parr shaker bottle and 2.3 grams (0.2 equiv.) of 5% Pd/C catalyst was added. Hydrogenation was carried out at 70° C. at 50 PSI until gas chromatography analysis determined that the reaction was complete. The solution was filtered through a layer of Hyflo super cel, and the filtrate isolated in each case. For Examples 1–5, the following table is indicative of the results obtained by the above process.

Tropanamine-HCL was isolated from the aqueous hydrogenation mixture by the following procedure: After dissolving sodium chloride (~30 g) in the aqueous solution, the pH was adjusted to 13 using 50% NaOH. The basic solution was extracted with $CH_2Cl_2$ (2×200 ml). The combined $CH_2Cl_2$ layers were dried with $Na_2SO_4$ and concentrated. The crude tropanamine in $CH_2Cl_2$ (50 ml) was cooled to 0° C. and with vigorous stirring gaseous HCl was slowly bubbled through the solution for 15–20 minutes. The white precipitate was collected by filtration.

| Example Number | Yield (%) | Ratio of endo:exo |
|---|---|---|
| 1. | 82.6 | 15.5/1 |
| 2. | 89 | 14/1 |
| 3. | 83.3 | 27/1 |
| 4. | 84.8 | 50/1 |

Endo/exo ratio was measured by GC In-process Assay: Conditions for the GC In-Process Assay Procedure are as follows:

Column: CAM (15 M×0.32 μm id×0.25 μm film)

Flow: 2.0 mL/min at 35° C.

Temperature Program:

Initial Temp.: 100° C.

Initial Time: 1 minute

Rate: 5° C./minute

Final Temp.: 220° C.

Final Time: 5 minutes

Injection Type: Split 15:1 Volume: 1.0 μL

Injector Temp.: 220° C.

Detector Type: FID Temp.: 220° C. Range: 0 Attn.: 0

Integrator Type: HP3396 Attn.: 2 PW: 0.04 ArRej.: 0

TRSH: 0

Run Time: 30 minutes

Sample Preparation

Reductive Amination Reaction:

Pipette 1 ml of reaction mixture into a 25 mL volumetric flask.

Dilute to volume with methanol.

Hydrogenolysis in Water:

Remove a small sample (2 mL) using a pipette. Filter this sample using a syringe filter. Pipette 0.5 mL of the filtered reaction mixture into a 25 mL volumetric. Add two drops of 50% NaOH solution. Dilute to volume with methanol.

Retention Times

Benzylamine: 4.39 min.

endo-Tropanamine: 5.00 min.

exo-Tropanamine: 5.51 min.

Tropinone: 6.62 min.

endo-Benzyltropanamine: 21.59 exo-Benzyltropanamine: 22.32

Benzylimine: 24.2 min.

I claim:

1. A process for stereoselectively preparing a compound of the formula

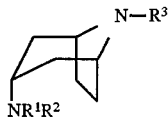 (I)

wherein $R^1$ and $R^2$ are independently phenyl, $C_1$–$C_4$ alkyl, phenyl-$C_1$–$C_4$ alkyl or hydrogen, provided that no more than one of R and $R^2$ is hydrogen, and wherein phenyl groups are substituted with 0–2 $C_1$–$C_3$ alkyl or $C_1$–$C_3$ alkoxy groups; $R^3$ is hydrogen, a nitrogen protecting group, phenyl, $C_1$–$C_3$ alkyl, or phenyl-$C_1$–$C_3$ alkyl, wherein phenyl groups are substituted with 0–2 $C_1$–$C_3$ alkyl or $C_1$–$C_3$ alkoxy groups; comprising the steps of a) providing a quantity of a compound of the formula

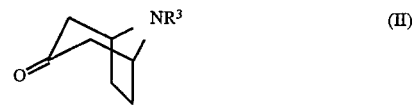 (II)

b) reducing the compound of formula II with an amine of the formula $HNR^1R^2$ in the presence of a triacyloxy borohydride salt of the formula $NaBH(OR^4)_3$ to form the endo-isomer of the compound of formula I, wherein $R^4$ is $C_4$–$C_{10}$ α-branched alkanoyl.

2. A process of claim 1 wherein the compounds of formulae I and II are compounds wherein $R^3$ is $C_1$–$C_3$ alkyl or a nitrogen protecting group.

3. A process of claim 2 wherein the compounds of formulae I and II are compounds wherein $R^1$ and $R^2$ are hydrogen or phenyl-$C_1$–$C_4$ alkyl.

4. A process of claim 1 wherein $R^4$ in the triacyloxy borohydride salt is 2-ethylhexanoyl or 2-ethylbutanoyl.

5. A process of claim 3 wherein the compound of formula I is a compound wherein $R^1$ is hydrogen, $R^2$ is benzyl and $R^3$ is methyl.

6. A process of claim 1 wherein the product of formula I is further reacted to remove $R^1$ and $R^2$ groups which are other than hydrogen.

7. A process of claim 6 wherein $R^3$ in formulae I, II and III is methyl, $R^1$ in the compound of formula I is hydrogen and $R^2$ in the compound of formula I is benzyl.

8. A process of claim 7 wherein the compound of formula I is treated by hydrogenolysis to remove the benzyl group.

* * * * *